United States Patent [19]

Guess et al.

[11] Patent Number: 4,462,255

[45] Date of Patent: Jul. 31, 1984

[54] PIEZOELECTRIC SCANNING SYSTEMS FOR ULTRASONIC TRANSDUCERS

[75] Inventors: Joe F. Guess, Littleton; Thomas R. Kruer, Aurora, both of Colo.

[73] Assignee: Technicare Corporation, Cleveland, Ohio

[21] Appl. No.: 463,413

[22] Filed: Feb. 3, 1983

[51] Int. Cl.³ ............................................. G01N 29/00
[52] U.S. Cl. ................................................. 73/633
[58] Field of Search ..................... 73/633; 128/660; 310/334, 336

[56] References Cited

U.S. PATENT DOCUMENTS

| | | | |
|---|---|---|---|
| 2,137,188 | 11/1938 | Whitman | 396/119 |
| 3,110,824 | 11/1963 | Flanagan | 310/330 |
| 3,271,527 | 9/1966 | Hammond | 369/144 |
| 4,339,682 | 7/1982 | Toda | 310/321 |
| 4,399,703 | 8/1983 | Matzuk | 73/633 X |
| 4,418,698 | 12/1983 | Dory | 73/633 X |
| 4,426,886 | 1/1984 | Finsterwald | 73/633 |

*Primary Examiner*—Donald O. Woodiel
*Assistant Examiner*—Vincent P. Koualick
*Attorney, Agent, or Firm*—W. Brinton Yorks, Jr.

[57] ABSTRACT

An ultrasonic scanning system is provided in which an ultrasonic transducer is oscillated for scanning purposes by a piezoelectric bender. One end of the bender is fixedly mounted in a sector scanner head, while the other end is connected to the ultrasonic transducer. The bender is deflected through the application of a drive voltage to electrodes plated on the piezoelectric material, causing the bender to deflect by a distance which is proportional to the applied voltage. The transducer is thereby caused to oscillate or rock by the motion of the bender.

18 Claims, 10 Drawing Figures

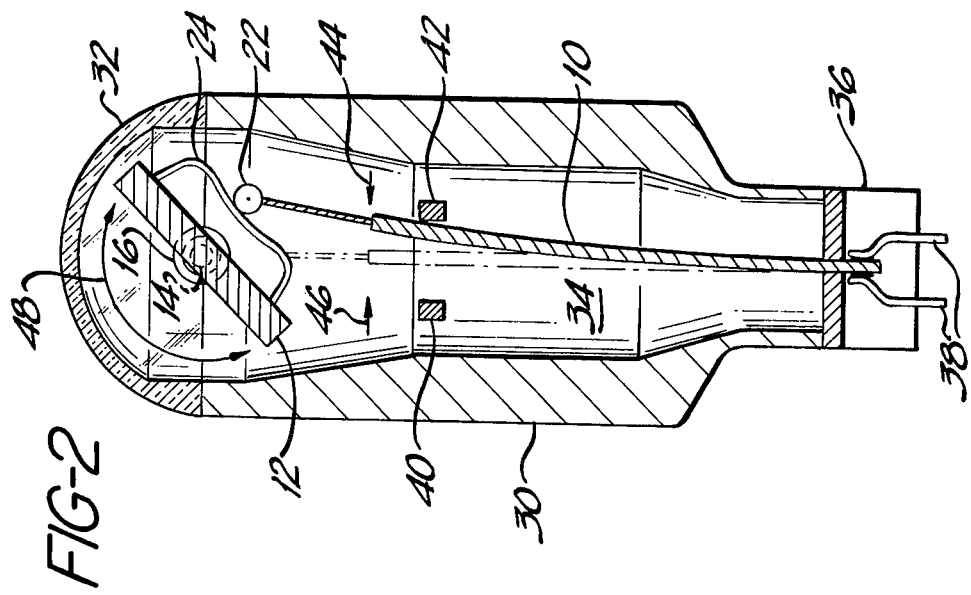
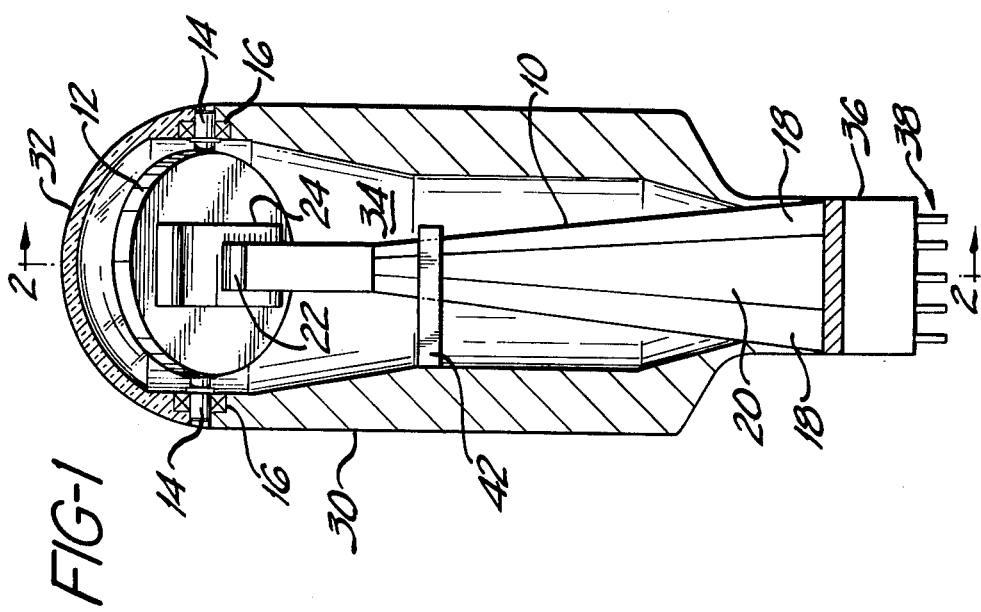

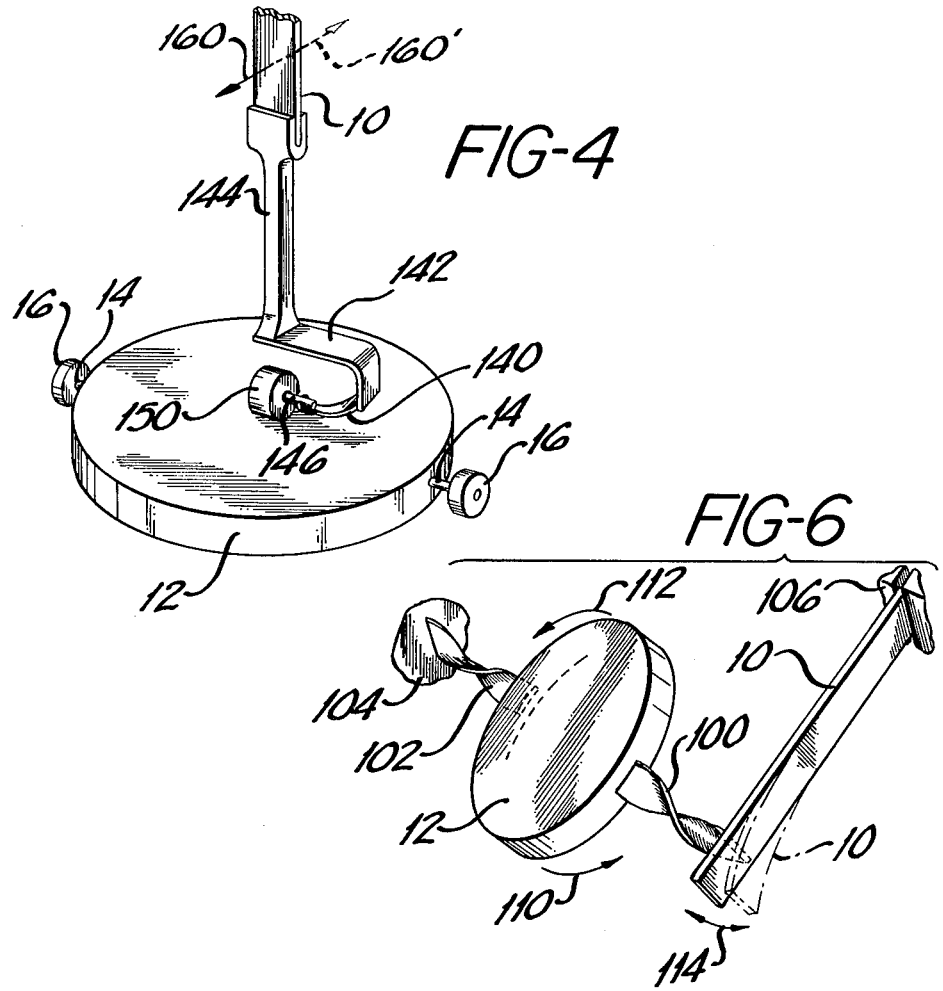
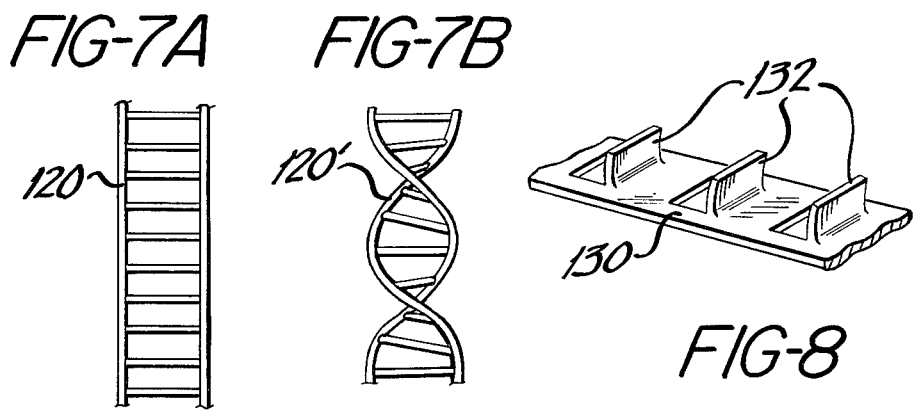

PIEZOELECTRIC SCANNING SYSTEMS FOR ULTRASONIC TRANSDUCERS

This invention relates to scanning systems for ultrasonic transducers and, in particular, to the use of a piezoelectric devices for scanning ultrasonic transducers.

Ultrasonic transducers are used to scan tissue in ultrasound nonintrusive diagnostic imaging system. In a typical ultrasound imaging system, a scanning probe containing a transducer is moved along the body of a patient. The transducer, or a reflector in line with the transducer, is oscillated back and forth to sweep the beam of energy produced by the transducer in an arc through the tissue of the patient. The ultrasonic energy is reflected by the tissue, with the reflection echoes being received by the transducer. The reflection information is then stored and processed to produce an image representative of the tissue material.

In order to oscillate the transducer or the reflector, the scanning probe typically includes a motor and a drive system, which may include a shaft, belt or geartrain. One such arrangement is shown in U.S. Pat. No. 4,330,874, entitled "Mechanical Sector Scanner Head and Power Train". In the system there shown, a shaft of the motor is connected by a belt to the shaft of an ultrasonic reflector, which is oscillated to sweep the reflected ultrasonic beam through a tissue sector. This system, like most others, also includes an encoder which provides positional information from the motor. The motor positional information is used to determine the position of the reflector, which enables coordination of the direction of the ultrasonic beam and the recovered reflection information relative to the tissue being scanned. In the arrangement of the aforementioned U.S. patent, the encoder is an optical wheel type encoder, but a Hall effective switch type shaft encoder can also be employed.

The motor and its associated drive train and encoder occupy the majority of the volume of the sector scanner head shown in the aforementioned U.S. patent, and also comprise a majority of its weight. Many ultrasonic examinations require that the scanning probe be small enough to allow access through restricted apertures in the patient. In addition, user fatigue during long examinations becomes a problem when the user must work with a relatively heavy scanning probe. Hence, it is desirable for a scanning probe to be constructed so as to be as small and light weight as possible, while retaining favorable performance characteristics. Phased array transducers have been developed which provide a small, light weight probe with a small aperture. However, due to their elaborate transducer and control electronics, such arrangements have proven to be relatively expensive.

Moreover, the frequency and transducer aperture of such phased array transducers are normally fixed at the time of manufacture. Due to the varying acoustical characteristics of patient tissue and the differing depths at which abnormalities under study can be found in the body, it is frequently desirable to change the focal aperture or the frequency of the scanning probe, often in the middle of an examination. Thus, it is desirable for a scanning probe to be constructed so as to facilitate a quick and simple change of the transducer frequency and aperture.

In accordance with the principles of the present invention, an ultrasonic scanning system is provided in which an ultrasonic transducer is oscillated for scanning purposes by a piezoelectric bender. One end of the bender is fixedly mounted in a sector scanner head, while the other end is connected to the ultrasonic transducer. The bender is deflected through the application of a voltage to electrodes plated on the piezoelectric material, causing the bender to deflect by a distance which is proportional to the applied voltage.

In accordance with the principles of a further aspect of the present invention, means are provided for translating the deflecting motion of the piezoelectric bender into rotational motion of the ultrasonic transducer. In one embodiment, the translating means includes a spring which connects the piezoelectric bender to the ultrasonic transducer. By appropriate choice of the stiffness of both the bender and the spring, and the static force of the spring, the bender stiffness can be effectively neutralized. In another embodiment of the present invention the translating means further includes a pivot for mounting the ultrasonic transducer. The motion of the piezoelectric bender causes oscillation of the transducer about the pivot. The degree of deflection of the piezoelectric bender, and hence the angle of oscillation of the ultrasonic transducer, may be determined by a separate electroded area provided on the piezoelectric bender or a separate parallel bender in the same plane from which a signal may be derived to indicate the position of the transducer.

The side-to-side movement of the piezoelectric bender of the present invention, which is the distance the end of the bender is displaced relative to its nominal position, is typically very small relative to the desired angular rotation of the ultrasonic transducer. Accordingly, it is desirable to provide an arrangement by which the relatively small displacement of the piezoelectric bender is translated simply and controllably into relatively much greater angular displacement by the ultrasonic transducer.

In accordance with the principles of a further aspect of the present invention, the relatively small linear displacement of the piezoelectric bender is converted simply into a relatively large angular displacement of an ultrasonic transducer or reflector. A transducer or reflector is located between a laterally moving area of the piezoelectric bender and a rigid surface of the scanner head. The ultrasonic emitter is held in place by a spiral-shaped rotator such that lateral movement by the piezoelectric bender imparts a change in tension to the spiral-shaped rotator. The change in tension causes the rotator to twist, which in turn produces a net torque on the emitter for oscillating the emitter. The resulting operation translates a relatively small linear movement of the piezoelectric bender into a relatively large angular movement by the ultrasonic emitter.

In accordance with the principles of a preferred embodiment of the present invention, the rotator comprises a ladder-like strip of tensile material which has been twisted into a spiral shape. The ladder-like shape does not exhibit a continuous strip of material along the center line of the rotator, which, if present, would undesirably be in compression in the spiral rotator.

In the drawings:

FIG. 1 illustrates a partial cross-sectional view of the scan head of a piezoelectric scanning system constructed in accordance with the principles of the present invention;

FIG. 2 illustrates another partial cross-sectional view of the scan head of FIG. 1 rotated by ninety degrees;

FIGS. 3A and 3B and 4 illustrate techniques for connecting a piezoelectric bender to a transducer with a spring in accordance with the principles of the present invention;

FIG. 6 illustrates the use of a rotator for connecting a transducer to a piezoelectric bender in accordance with the principles of the present invention; and FIGS. 7A and 7B and 8 illustrate details of the rotator of FIG. 6.

Figure 3A:
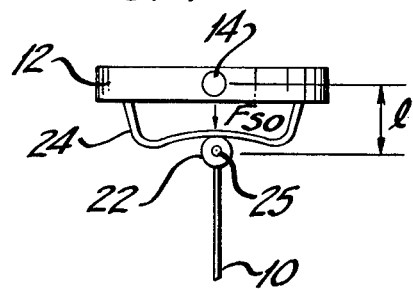

Referring to FIG. 1, an ultrasonic transducer scan head constructed in accordance with the principles of the present invention is shown in partial cross section. A piezoelectric bender 10 is located in a housing 30. The piezoelectric bender 10 is clamped at one end of the housing by a base 36 which also holds electrodes 38 in contact with the broad end of the bender 10. A transducer 12 is mounted by a pivot 14 at the upper end of the housing. Flexible alloy wiring (not shown) carries signals to and from the transducer. The pivot 14 rotates in bearing assemblies 16. Ultrasonic energy produced by the transducer 12 is directed through an acoustically transparent aperture or membrane 32 at the upper end of the housing, which may be made of a plastic material. The piezoelectric bender 10 is connected to the back of the transducer 12 by a spring 24 and a spring pivot 22. Turnaround springs 40 and 42, one of which is shown in FIG. 1, extend from the side of the interior of the housing 30 on either side of the piezoelectric bender 10. The interior of the housing 30 is filled with an acoustic coupling fluid 34. Another partial cross sectional view of the scan head of FIG. 1 is shown in FIG. 2, rotated by ninety degrees with respect to the view of FIG. 1.

The piezoelectric bender 10 includes electrodes 18 plated on the front and back surfaces of the bender. These electrodes are electrically connected to plug-in electrodes 38, which extend from the base 36. When a voltage is applied between the electrodes on the two sides of the bender, the bender is caused to bend or generate a force in proportional to the applied voltage. The degree of bending is detected by a separate, tapered center electroded area 20, which extends along the center of the bender. The center electrode 20 thus produces a voltage at one of the electrodes 38 which can be used to indicate the position of the transducer. Alternatively, a separate bender can be clamped in the same plane as bender 10. The separate bender will then move in unison with the bender 10, producing a position-representative output signal which is electrically isolated from the drive signals applied to the bender 10.

A voltage is applied between the electrodes 18 on the front and back surfaces of the piezoelectric bender 10. The necessary voltage is that which achieves a substantially constant bender velocity by overcoming frictional forces within the assembly. The voltage causes the bender 10 to deflect toward one side of the enclosure 30 in FIG. 2, with the end of the bender pivoting around the pivot 22 and the transducer 12 pivoting around its pivot 14. The upper face of the transducer 12 will then move from a position where it is facing upward in the FIGS. 1 and 2 to a position where the face is oriented approximately 45 degrees from the upward axis. The motion of the face of the transducer 12 is indicated by the arrow 48 in FIG. 2. When the transducer 12 reaches its approximate 45 degree orientation, the sense of the voltage is reversed to scan the transducer in the opposite direction. The direction of the bender is reversed when the bender 10 reaches one of the extremes of deflection indicated by arrows 44 and 46 in FIG. 2, with the illustrated bender exhibiting a typical displacement of approximately one-eighth inch at the free end.

The electrically motivated reversal of the bender direction is aided by turn-around springs 40 and 42 shown in FIGS. 1 and 2. As the sense of the ramping voltage applied to the bender 10 reverses, the bender 10 is also contacting one of the turn-around springs 40 and 42, which mechanically aids the reversal of the direction of the bender. In addition, it is desirable to place the turn-around springs at the node of the next excited frequency of the arrangement to prevent undesired oscillations. In a particular embodiments, for instance, it was desired to scan at a 15 Hz rate and the system exhibited a resonant frequency at approximately 200 Hz. The vertical placement of the turn-around springs along the length of the bender was adjusted to prevent oscillation at 200 Hz. This is done experimentally, with the positioning varying with the length of the bender. Alternatively, the turn-around springs may be placed at the extremes of the path traversed by the transducer, as shown by springs 70 and 72 in FIG. 5.

The stiffness of the bender 10 will cause a variation of the angular velocity of the oscillating transducer as a function of angle. By appropriate choice of the static force exerted by the spring 24, and its stiffness, the bender stiffness can be effectively neutralized.

FIG. 3A shows the transducer 12, the spring 24, and the bender 10 in the undeflected position. In this position, the end of the bender at pivot 22 slightly compresses the spring 24 from its normal U-shape, whereby the spring 24 will exert a downward directed static force indicated by arrow $F_{so}$. With the stiffness of the bender expressed as a constant $k_b$, the angular velocity of the transducer will be least affected around its undeflected position by the static force and bender stiffness combination if $F_{so}=k_b l$ where l is the moment arm shown in FIG. 3A. The arrangement will exhibit an almost constant velocity over a ±45 degree sector scan reference to the undeflected position, when $k_s = -k_b$ where $k_s$ is the stiffness of the spring. In addition, the spring 24 will absorb the thermal expansion and contraction of the components in the arrangement when the scan head experiences temperature changes.

Figure 3B:
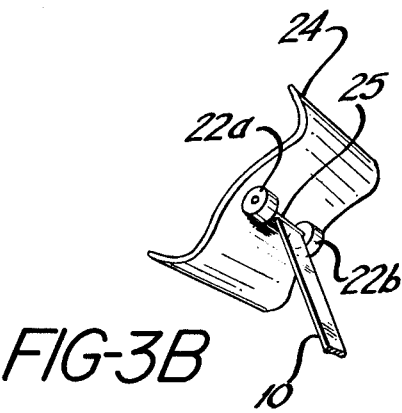

An arrangement for connecting the piezoelectric bender 10 to the pivot point 22 on spring 24 is shown in FIG. 3B. There, the end of the piezoelectric bender 10 is connected to a shaft 25. The ends of the shaft 25 pass through two bearing assemblies 22A and 22B, which are fastened to the spring 24. The bender 10 and shaft 25 are then free to pivot in the bearings 22A and 22B.

Another embodiment of the present invention which utilizes a cantilevered spring arrangement is shown in FIG. 4. Unlike the embodiment of FIGS. 1 and 2, a pivot point is located between the spring and the transducer in FIG. 4 instead of between the bender and the spring.

In FIG. 4, a piezoelectric bender 10 is connected at its unclamped end to a plastic extender 144. The plastic extender 144 is considerably tapered as compared with the bender 10 to afford a lessening of the force required to move through the acoustic fluid in a scan head. The end of the extender 144 remote from the bender 10 is connected to a rigid metal spring mounted 142. A relatively thin spring 140 is connected between the spring mount 142 and a shaft 146, located in a pivot point bearing assembly 150. The bearing assembly 150 is secured to the back of the transducer 12 and is vertically aligned with the extender 144 in FIG. 4. As in FIGS. 1 and 2, the transducer 12 is mounted between shafts 14 which are located in bearing assemblies 16 on either side of the transducer.

As the piezoelectric bender 10 moves back and forth as indicated by arrows 160 and 160', the shaft 146 rotates in the bearing assembly 150. The face of the transducer 12 thereby scans a subject. The axes of shafts 146 and 14 are in parallel to prevent binding as the transducer is oscillated.

The embodiment of FIG. 4 is governed by the static force equation given in conjunction with FIG. 3A, $F_{so}=k_b l$, as the cantilevered spring mount and spring exert a static force in the vertical direction in FIG. 4. Unlike the embodiment of FIG. 3A, the bender stiffness will be neutralized when the spring 140 of FIG. 4 exhibits a positive constant of stiffness, and $k_s = k_b$.

Figure 5:
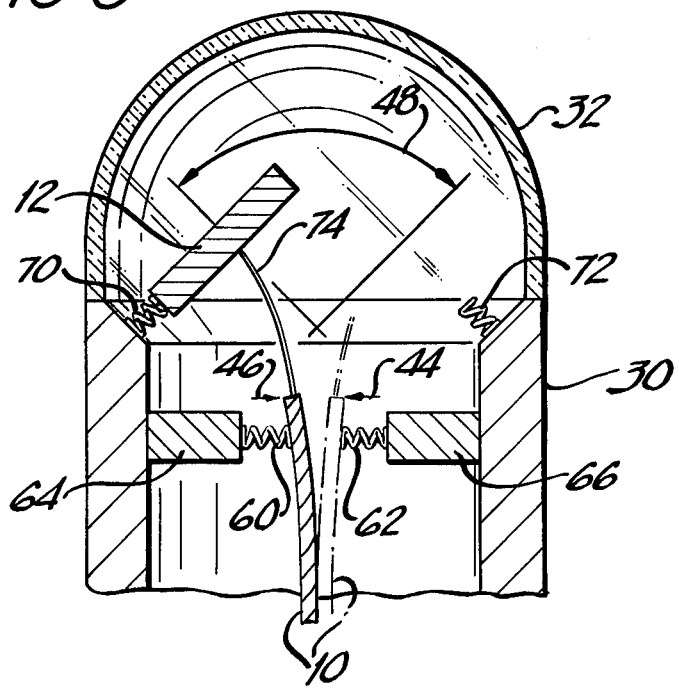
FIG. 5 illustrates a further technique for connecting a piezoelelctric bender to a transducer in accordance with the principles of the present invention.

A further embodiment for connecting a piezoelectric bender to the transducer is shown in the partial cross-sectional view of the scan head of FIG. 5. In this embodiment, the piezoelectric bender 10 is connected to the transducer 12 by a leaf spring 74. The piezoelectric bender 10 moves back and forth between limits indicated by arrows 44 and 46, and reversal of the bender direction is aided by turn-around springs 60 and 62, mounted on spring mounts 64 and 66 at the sides of the interior of the scan head. In addition, turn-around springs 70 and 72 are provided for the transducer 12 itself at either side of the transducer path in the scan head. In this embodiment, the transducer 12 oscillates back and forth around an effective center of rotation indicated at the "X" shown in FIG. 5. This center of rotation is seen to be behind the back surface of the transducer 12.

Another embodiment for translating the essentially linear translation of a piezoelectric bender into rotational movement of a transducer is shown in FIG. 6. In FIG. 6, the piezoelectric bender 10 is clamped at one end by a clamp 106. A transducer 12 is connected between the free end of the piezoelectric bender 10 and a wall 104 of the scan head housing by a twisted rotator 100 and a torsion spring 102. The torsion spring 102 balances the static torque produced by the rotator 100. In its static position, the transducer is tilted in its +45 degree orientation. As the free end of the piezoelectric bender 10 moves back and forth in an essentially linear manner as indicated by arrow 114, the rotator 100 and torsion spring 102 are alternately untwisted and retwisted. This produces oscillation of the transducer 12 as indicated by directional arrows 110 and 112 as the transducer is twisted through its 0 degree orientation to its −45 degree orientation and back. The embodiment of FIG. 6 provides relatively large angles of rotation of the transducer 12 in response to relatively small linear translation of the piezoelectric bender 10.

The embodiment of FIG. 6 is advantageous also in that, since there are no bearings required to support the rotating system, bearing wear and friction are not considerations in system reliability. There is virtually no wear in the system, and if the piezoelectric bender 10, the torsion spring 102 and the rotator 100 are not used beyond their fatigue limits, the life of the system is virtually indefinite.

A simple strip of resilient material could be used for the torsion spring and rotator in FIG. 6, but such a construction would be undesirable because the material would be in compression along the center line of the strip when the strip is twisted. A preferred way of constructing the rotator and torsion spring is to fabricate a "ladder" 120 of wire, as shown in FIG. 7A. The ladder 120 is then twisted to form the spiral rotator or torsion spring 120', as shown in FIG. 7B.

A structure similar to the ladder 120 of FIG. 7A may be constructed from a strip of resilient material as shown in FIG. 8. In FIG. 8, a strip of material 130 is punched to form flaps 132 along its length. The upwardly folded flaps 132 not only remove material from the center portion of the strip, but also stiffen the cross member sections running across the strip 130 between the flaps 132. The punched strip is then twisted to form the rotator 100 or the torsion spring 102.

Because embodiments constructed in accordance with the principles of the present invention require no motors or shaft encoders for determining the position of the transducer, such scan heads may be constructed simply and inexpensively. A user can purchase a number of such sealed fluid scan heads, using them interchangeably with a unit containing the necessary electronics to deflect the bender and read the position signal from the piezoelectric sensor. Thus, a user can easily interchange scan heads having differing frequency and aperture characteristics.

What is claimed is:

1. In an ultrasonic diagnostic imaging system, apparatus for scanning the tissue of a patient, comprising:
   a fluid-filled chamber, including an acoustically transparent aperture for passing ultrasonic energy;
   a source of ultrasonic excitation energy;
   ultrasonic energy transmission means, located in said chamber, and including an ultrasonic transducer responsive to said excitation energy, for producing a beam of ultrasonic energy which is directed toward said aperture;
   a source of oscillation potential; and
   a piezoelectric bender, located in said chamber and connected to said ultrasonic energy transmission means, and responsive to said oscillation potential for deflecting said bender to cause scanning of said beam of ultrasonic energy through said aperture.

2. The arrangement of claim 1, further comprising:
   a spring, coupled between said piezoelectric bender and said ultrasonic energy transmission means,
   wherein the scanning velocity of said beam is a function of the stiffness of said spring.

3. The arrangement of claim 1, wherein said ultrasonic energy transmission means further comprises a pivot for mounting said ultrasonic transducer within said chamber,
   wherein movement by said piezoelectric bender is translated to said transducer so as to cause said transducer to oscillate about said pivot.

4. The arrangement of claim 2, wherein said bender is mounted at one end within said chamber, and said spring is connected between the other end of said bender and said ultrasonic transducer.

5. The arrangement of claim 4, wherein said other end of said bender is connected to said spring by a pivot.

6. The arrangement of claim 1, wherein said piezoelectric bender includes an electroded area for providing a signal representative of the position of said beam of ultrasonic energy.

7. The arrangement of claim 4, further comprising first and second turn-around springs located within said chamber on respectively opposite sides of said bender for limiting the excursions of said other end of said bender.

8. In an ultrasonic diagnostic imaging system, an ultrasonic scanner comprising:
   a hollow chamber;
   an ultrasonic transducer, pivotally mounted within said chamber; and
   a piezoelectric bender, fixedly mounted at a first end and connected to said ultrasonic transducer at a second end, and responsive to an excitation potential for moving said transducer in a scanning manner.

9. In an ultrasonic diagnostic imaging system, an ultrasonic scanner comprising:
   an enclosure;
   an ultrasonic transducer pivotally mounted within said enclosure;
   a piezoelectric bender fixedly mounted at a first end within said enclosure, and having a second end;
   a cantilevered spring mount connected to said second end of said piezoelectric bender and nominally located in a plane normal to the longest dimension of said piezoelectric bender;
   a pivot fixedly connected to the back side of said transducer; and
   a spring connected between said cantilevered spring mount and said pivot.

10. The arrangement of claim 9, wherein said pivot includes a shaft mounted in a bearing, said bearing being connected to the back side of said transducer and said spring being connected to said shaft.

11. The arrangement of claim 10, further comprising an extender connected between said second end of said piezoelectric bender and said cantilevered spring mount, said extender having a width which is less than the width of said piezoelectric bender.

12. In an ultrasound diagnostic imaging system, apparatus for producing a scanning beam of ultrasonic energy comprising:
   a fluid-filled chamber;
   a source of excitation potential;
   an ultrasonic transducer, located in said chamber and responsive to said excitation potential, for producing ultrasonic energy;
   a source of scanning potential;
   motive means, located in said chamber, and responsive to said scanning potential for producing motion which is to be translated to said transducer; and
   a flexible, spiral-shaped rotator connected, together with said transducer, in line between said motive means and an anchor point within said chamber,
   wherein motion by said motive means causes a change in the tension of said rotator and imparts a net torque to said transducer, whereby said transducer is caused to oscillate.

13. The arrangement of claim 12, wherein said rotator comprises a twisted ladder-like strip of tensile material.

14. The arrangement of claim 13, further comprising a torsion spring, wherein said transducer is connected by said torsion spring and said rotator between said motive means and said anchor point.

15. The arrangement of claim 14, wherein said motive means includes a piezoelectric bender having a first end region fixedly mounted within said chamber and a second end region connected to said transducer by said rotator.

16. The arrangement of claim 14, wherein said torsion spring and said rotator are twisted in respectively opposite directions.

17. The arrangement of claim 12, wherein said rotator comprises a slotted and twisted strip of tensile material.

18. The arrangement of claim 17, wherein said slots are formed by the outward folding of flaps from said strip of tensile material.

* * * * *